(12) United States Patent
Gorelik et al.

(10) Patent No.: US 8,758,687 B2
(45) Date of Patent: Jun. 24, 2014

(54) FLUID DELIVERY SYSTEM AND APPARATUS TO PERFORM THE SAME

(75) Inventors: Gregory Gorelik, Newton, MA (US); Rus Yukhananov, Mansfield, MA (US)

(73) Assignee: Precision Biosystems, Mansfield, MA (US)

( * ) Notice: Subject to any disclaimer, the term of this patent is extended or adjusted under 35 U.S.C. 154(b) by 0 days.

(21) Appl. No.: 13/641,473

(22) PCT Filed: May 6, 2011

(86) PCT No.: PCT/US2011/035480
§ 371 (c)(1),
(2), (4) Date: Dec. 5, 2012

(87) PCT Pub. No.: WO2011/140422
PCT Pub. Date: Nov. 10, 2011

(65) Prior Publication Data
US 2013/0202487 A1 Aug. 8, 2013

Related U.S. Application Data

(60) Provisional application No. 61/331,861, filed on May 6, 2010.

(51) Int. Cl.
*G01N 15/06* (2006.01)

(52) U.S. Cl.
USPC .......... 422/68.1; 422/500; 422/501; 422/502; 422/503; 422/504; 422/536; 422/537; 422/538; 436/180

(58) Field of Classification Search
USPC ............ 422/68, 50, 500–504, 536–538, 68.1; 222/251; 436/180
See application file for complete search history.

(56) References Cited

U.S. PATENT DOCUMENTS 3,719,087 A * 3/1973 Thiers ........................ 73/864.14

* cited by examiner

*Primary Examiner* — Jyoti Nagpaul (57) ABSTRACT

The present invention is an apparatus and fluid delivery system for automated assays. The apparatus, for example, may be used for western blotting that uses flow lines for multiple reagents. In one embodiment, the present invention comprises a tray base with one or more fixed or disposable trays for testing samples, multiple flow lines, and multiple valves and the system is used for automatic controlled delivery of different fluids from supply vessels to different trays and discharges them to designated reservoirs or sewage system with minimum of operator actions. The system may include air line to assist supply and discharge the fluids and also coupled with measuring vessels with adjustable volume and valves adapted to interface with a valve operating unit with drive means. The system is controlled by a programmable electronic device that controls the preset values and sequences of valves operation to deliver or discharge the selected fluids in any one or more of plural fluid input ports individually or all together simultaneously, by a set of programmable pinch valves assemblies that pinching or releasing multiple of elastomeric flow conduits, used as a pinch member. The valve operating unit may, in one embodiment, be a single drive unit to control all valve assemblies or, as alternative embodiment, attached to the housing individual mechanism.

15 Claims, 10 Drawing Sheets

FIG. 1

| 1. Programmed Cycle | 3. Air Pressure | 2. Valve Activation | | | |
|---|---|---|---|---|---|
| | | Liquid Supply Valves | Target Valves | Air Valves | Discharge Valves |
| 01. Rock or Shake Tray 7 | - | - | - | - | - |
| 02. Discharge Vessel 7.10 or 7.20 to 5.10 or 5.20, 5.30 or 5.40 | + | - | - | 2.45 | 2.31 or 2.32 2.33 or 2.34 |
| 03. Discharge Vessel 8.10 to fill up measure Chambers 9.10 or 9.20 | + | 2.21, 2.22 | - | 2.41, 2.47 | - |
| 04. Fill in Vessel 7.10 or 7.20 from 9.10 or 9.20 | + | 2.24 or 2.25 | - | 2.44, 2.46 | - |
| Repeat 02 | + | - | - | 2.45 | 2.31 or 2.32 2.33 or 2.34 |
| 05. Deliver content of 8.20 to 7.10 or 8.40 to 7.20 | + | - | 2.11 or 2.13 | 2.42, 2.46 | - |
| Repeat 02 | + | - | - | 2.45 | 2.31 or 2.32 2.33 or 2.34 |
| Repeat 03. | + | 2.21, 2.22 | - | 2.41, 2.47 | - |
| Repeat 02 | + | - | - | 2.45 | 2.31 or 2.32 2.33 or 2.34 |
| Repeat 04. | + | 2.24 or 2.25 | - | 2.44, 2.46 | - |
| Repeat 02 | + | - | - | 2.45 | 2.31 or 2.32 2.33 or 2.34 |
| 06. Deliver content of 8.30 to 7.10 or 8.50 to 7.20 | + | - | 2.12 or 2.14 | 2.42, 2.46 | - |
| Repeat 02, 03 and 04 | | | | | |
| Repeat 03 | + | 2.21, 2.22 | - | 2.41, 2.47 | - |
| 07. Fill in Vessels 8.20 and 8.30, or 8.40 and 8.50 from 9.10 and 9.20 | + | 2.23, 2.26 | - | 2.44, 2.43 | - |
| Repeat 05 and 06 | + | - | 2.11, 2.12, 2.12, 2.14 | 2.42, 2.46 | - |
| Repeat 07, 05, 06, 02, 03 according to test protocol | | | | | |

FIG. 5 Amended

FLUID DELIVERY SYSTEM AND APPARATUS TO PERFORM THE SAME

REFERENCE TO RELATED APPLICATIONS

This applications claims the benefit of and priority to U.S. Provisional Application Ser. No. 61/331,861 filed on May 6, 2010, which is hereby incorporated by reference, in its entirety, into this specification.

BACKGROUND OF THE INVENTION

The present invention relates to automated assay apparatus used to rapidly detect, for example, proteins, in the diagnosis of infection or diseases. Currently available automated assay apparatus are overly complicated and use a number of pumps and dispensers to deliver different liquid reagents to the reaction chambers.

U.S. Pat. No. 4,859,419 discloses an apparatus for immunoassay of multiple samples of biological fluids. The apparatus contains valved ports and a pump that delivers through a single conduit the same biological fluids to a plural of test vessels. The test vessels are closely connected to each other and share a single port to receive and discharge all biological fluids. Conventional assay apparatus of this type do not allow different liquid reagents to be applied to different test samples using different protocols for different test samples. Further, delivery of multiple liquid reagents through the same conduit lead to potential contamination between different liquid reagents that is not acceptable for most types of tests.

U.S. Pat. No. 5,567,595 discloses an automated blot assay apparatus. This apparatus comprises a rocking tray to assure a mixture of the reaction components and for draining simultaneously of all reaction chambers of a tray to remove solution. Thus requires using only one predetermined schedule for all reaction means. Each solution has its own pump and movable dispenser that makes the programming means and construction complex and requires special features to avoid cross-contamination of solutions. Also, for some assay procedure for better mixture of reagents and cover the test samples is preferable to use horizontal agitation of trays which is not possible by applying the method of draining reaction chambers by inclining the tray.

Valves are widely used for control the fluids flow through individually controlled passageways. For example solenoid controlled valves. To use them with different reagents and a numbers of reaction chambers requires dozens of individual valves results in complexity of control and programming means, to produce the apparatus and use them.

Pinch valves and flexible conduits also used in a wide range of apparatus. Some of the known prior art are designed either normally closed or normally open, the control function, accordingly, is to release or to close the passageway. In some applications, most critical for the valves function is the requirement that the passageway through the conduits should be completely open or close.

Other obstacles to use either type of valves is, that in some cases, due the physical properties of elastomeric conduits, different properties of fluids, and contamination, cause the passageway to close, partially or completely, restricting the flow. Also, with pinch valves, when necessary random activation of two or three sets of multiple pinch valves, there should be used multiple activators. This made the control system more complex and requires more space to place them in apparatus. The known prior art includes elastomeric flow conduits and different shapes of plungers or pistons. These require precise machining operations and quite expensive to produce. Some of the known multiple of pinch valves assemble having the multiple flexible flow conduits wherein the activating the pinch action of one of them impede the pinch state of their neighboring conduits and require special features to avoid this. In some of known multiple conduits pinch valves conduits are placed around or near the actuator, the length of the conduits directed to different sites is different and in some cases due the conduits length and liquid properties the valuable liquid will be waste.

SUMMARY OF THE INVENTION

One object of the present invention is the provision the possibility to perform the assay procedure for different testing samples with different time schedules simultaneously.

Another object of the present invention is the provision the possibility to apply to tray either horizontal or rocking agitations.

Another object of the present invention is the provision of better delivery and smaller amount of reagents necessary to perform the reaction.

Another object of the present invention is the provision of multiple pinch valves assemble that allows programmable activation of any number of pinch valves at a necessary sequence of open or close the passageway through the conduits.

Another object of the present invention is the provision of an improved multiple pinch valves assemble which is able to prevent the clogging of passageways through the conduits by completely releasing them during the not working time.

A further object of the present invention is the provision of an improved multiple pinch valves assemble having a simple, standard, and easy to acquire pinch members, to reduce the cost and time to produce parts and assembly the apparatus.

A further object of the present invention is the provision of an improved multiple pinch valves assemble having a simple actuator to open the passageway through the conduits by moving simultaneously multiple or individually one pinch member away from the conduits to facilitate the opening of the passageways.

Another objective of the present invention is the provision of improved multiple pinch valves assemble which controls opening or close of one flow conduits that not affects the opening or close the others.

Still another objective of the present invention is the provision of an improved multiple of pinch valves assembly having a motor and a multi track cam which handle fluids flow through the multiple conduits connected to the fluid sources is a compact device that combines the functions of one, two, or three multiple pinch valves assemblies.

In one embodiment, the present invention seeks to fulfill the need by providing apparatus with relatively fewer components and flexible operation. The invention comprises a tray with one or more fixed or disposable reaction chambers, means to activate tray's either horizontal or rocking agitation motion, multiple valves and automatic control system providing delivery the different fluids from supply vessels to different reaction chambers and discharging them to designated reservoirs according to individual predetermined schedule. The apparatus may include air lines to assist supply and discharge the fluids coupled with measuring vessels with adjustable volume. Valves are adapted to interface with a valve operating unit with drive means activating plural fluid input ports individually or all together simultaneously. The valve operating unit may, in one embodiment, be a single drive unit to control all valve assemblies or, as alternative embodiment, attached to the housing individual mechanism.

BRIEF DESCRIPTION OF THE DRAWINGS

The present invention will be more fully understood with reference to the accompanying drawings in which:

FIG. 5b is a fragmentary, perspective view of a portion of the conduits of three different sets, illustrating how the torsion springs placed and pinch the conduits of the assembly of FIG. 5a;

FIG. 5c is a prospective view of the multi track cam of the preferred embodiment of the present invention of FIG. 5a.

DESCRIPTION OF THE INVENTION

The present invention is directed to an automatic apparatus that comprises a multiple of liquid reagent vessels, washer vessels, variable volume measuring vessels, logic control unit, air supply lines, tray with one or multiple reaction chambers agitating either horizontally or rocking, multiple of elastomeric conduits connecting the supply and target vessels, controlled by multiple of pinch valves independently closing or releasing elastomeric flow conduits passageways.

Figure 1:
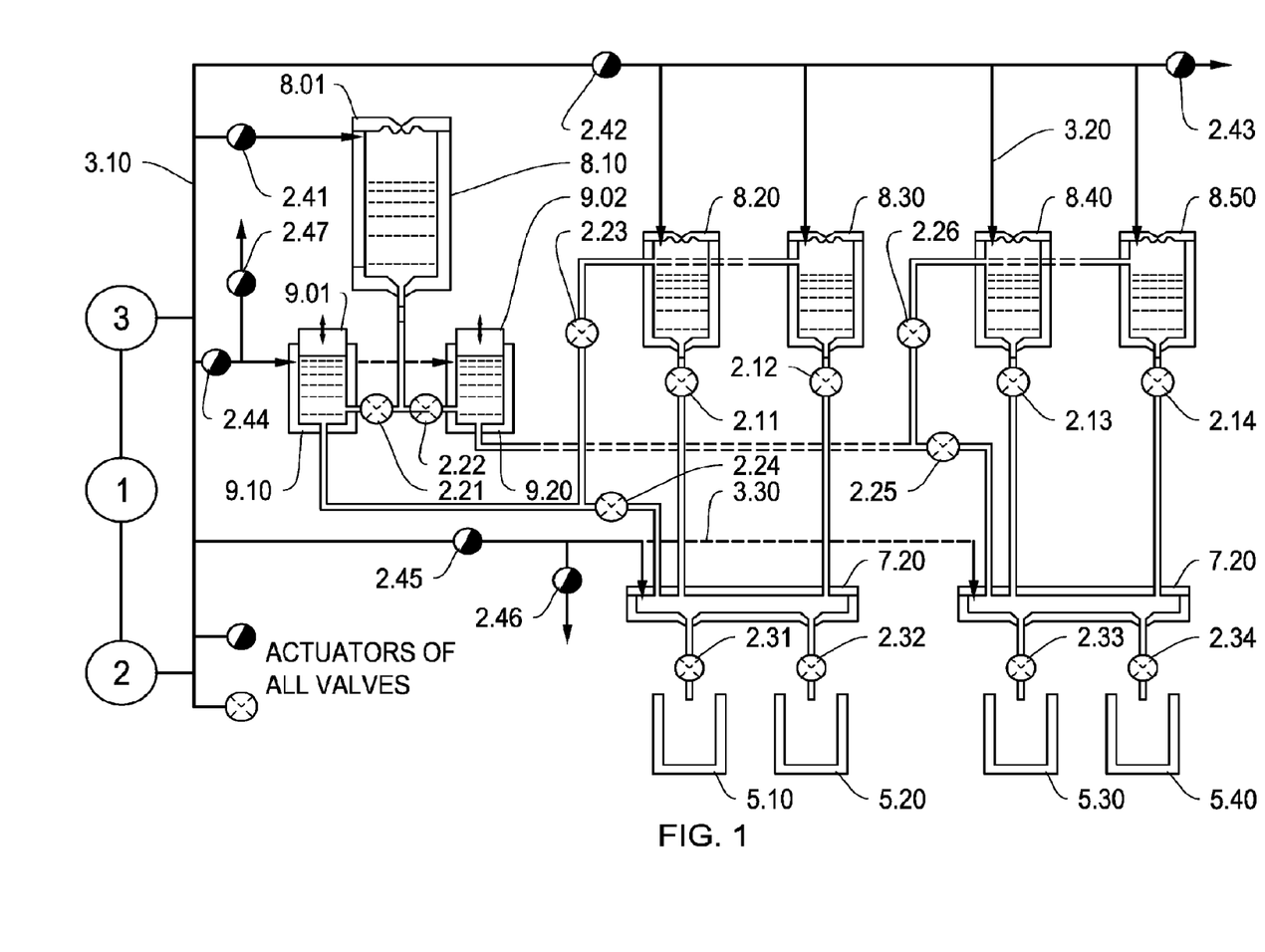
FIG. 1 is a schematic flow diagram of the complete system incorporating components comprising the one embodiment of the apparatus according to the present invention.

FIG. 1 discloses a schematic diagram of the complete system incorporating components comprising the one embodiment of apparatus according to the present invention whereby number 1 designated the logic control system, PLC, 2—a valve drive unit, and 3—air pressure supply unit. The following numbers are used to designate other parts of preferred embodiment: 2.11 to 2.14—reagents supply valves, 2.21 to 2.26—washer supply valves, 2.31 to 2.34—tray reaction chambers discharge valves, 2.41, 2.42, 2.44, 2.45—air pressure supply valves, 2.43, 2.46, 247—air pressure release valves, 5.10 to 5.40—liquid discharge vessels, 7.10 and 7.20—tray reaction chambers, 8.10—washer supply vessel, 8.20, 8.30, 8.40 and 8.50—reagent supply vessels, 9.10 and 9.20—variable volume measure vessels with 9.01 and 9.02—movable plungers to adjust the required volume of washer liquid, and 8.01 is sealing lids for all vessels.

Figure 2:
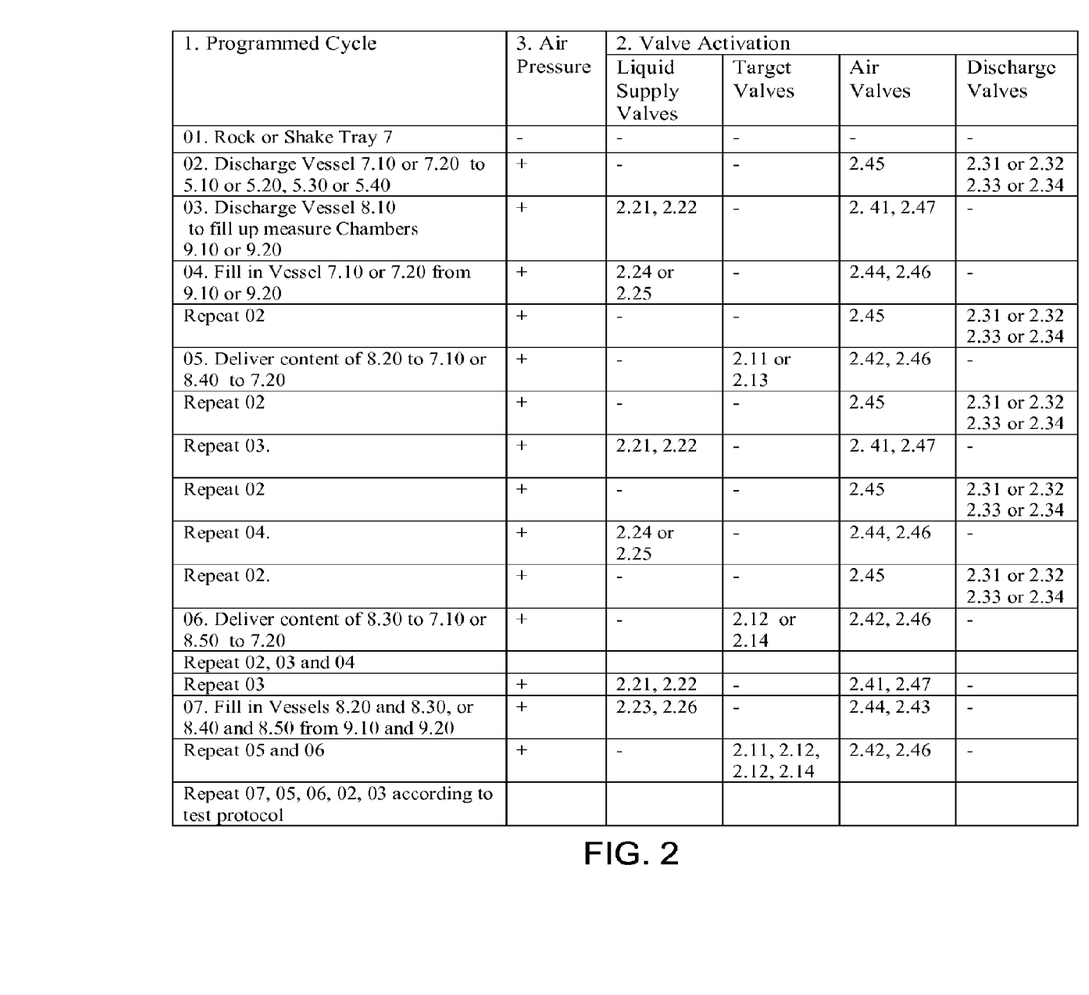
FIG. 2 is a table that shows the example of sequence of actions of one embodiment apparatus according to the present invention.

FIG. 2 illustrates one possible sequence for operating the apparatus. PLC 1 checks the initial state of the apparatus' components and if all components are ready, starts the process. In this case it is by activating the motor 6.40 (FIG. 6), starting the tray agitation, horizontal back-and-forth or rocking, and according to the schedule activate the valve drive to open the corresponding valves 2.31 or 2.33 to discharge the content of the reaction chambers 7.10 or 7.20. Simultaneously activated air valves 2.41 and 2.46 to supply air pressure to 8.10 and connect chambers 7.10 or 7.20 with atmosphere. Further, the table shows the complete schedule, cycle by cycle. There are may be programmed different scenarios.

Figure 3:
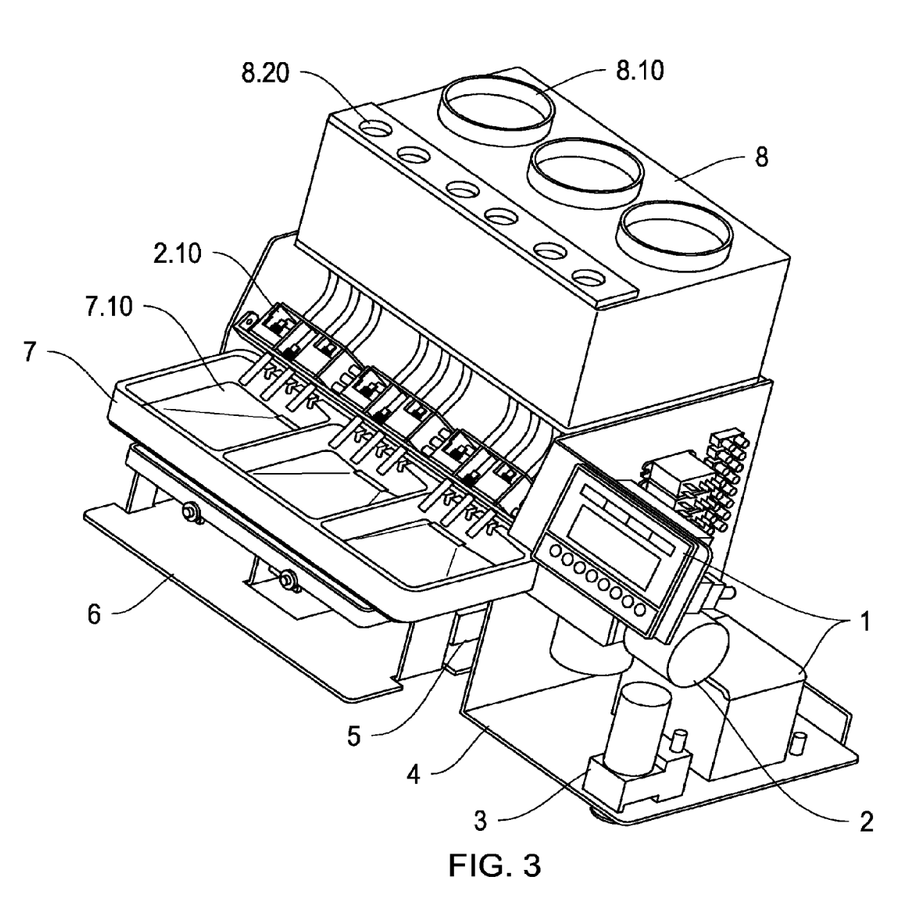
FIG. 3 is a perspective view of one embodiment of the apparatus according to the present invention. All covers removed.

FIG. 3 discloses the preferred embodiment of the major components of the apparatus. A tray 7 with three reaction chambers, one of them designated 7.10, is mounted on the tray platform of the agitating table, 6, that can alternatively be set up for a rocking or a shaking movement. A block of supply vessels 8 is divided on a separate isolated vessels containing washer liquid and a multiple of different reagents. The exemplary embodiment has three, designated 8.10, 8.20, 8.30—for washer, and six, 8.40 to 8.90,—for reagents. All control function are performed by PLC 1, and control circuit 1.20. The display unit 1.10 allows change of an existing program or the addition of new one. By 2 there designated the block of valves and valve drive mechanism, 2.10 is one of multiple valve assemblies. Air pump 3 mounted on base 4 supplies the air pressure to all vessels according to predetermined sequence. Under the tray 7 is placed a number of discharge vessels 5. The number of discharge vessels depends on number of reaction chambers, number of different reagents, and the number of reagents desirable to collect.

Figure 4:
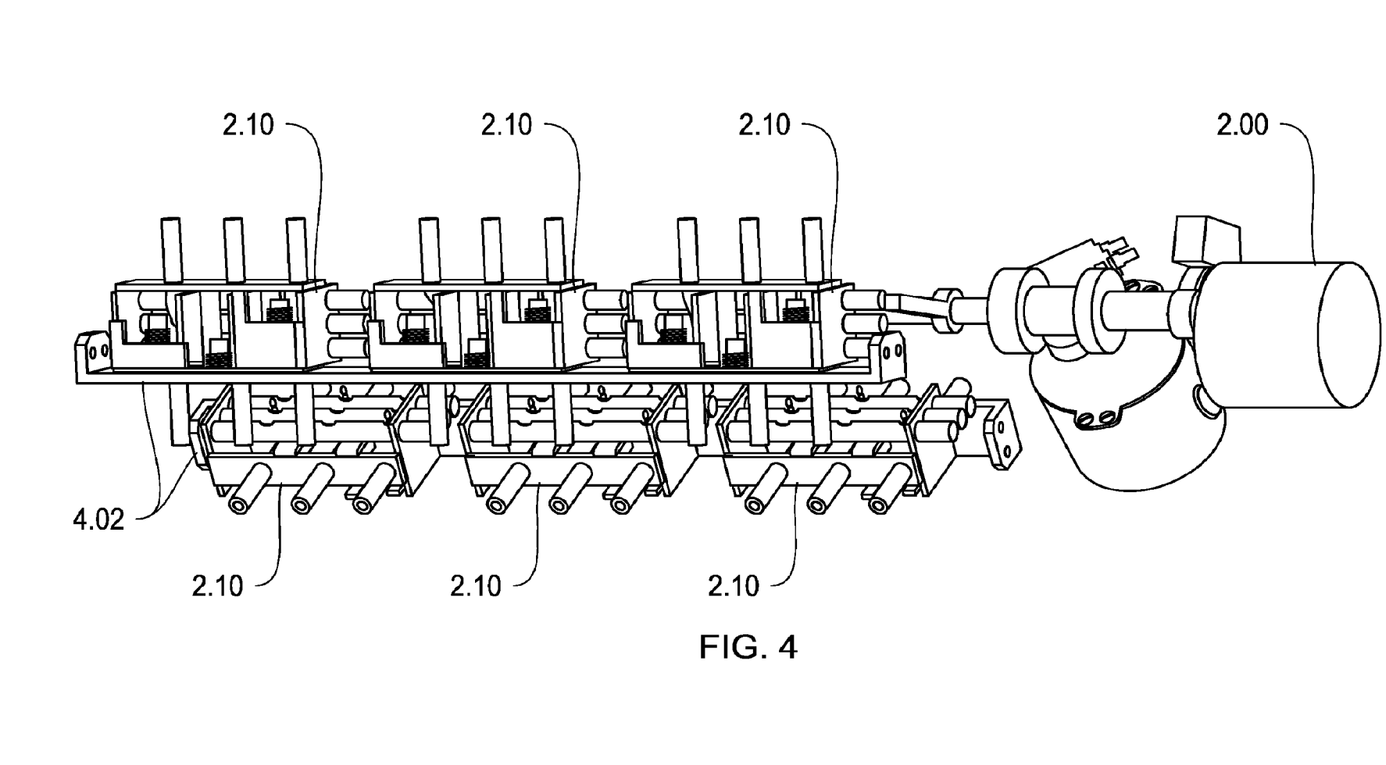
FIG. 4 is a perspective view of one embodiment of a multiple of programmable pinch valves assemblies of 6 blocks of three pinch valves assemblies used with a single drive unit.
Figure 4A:
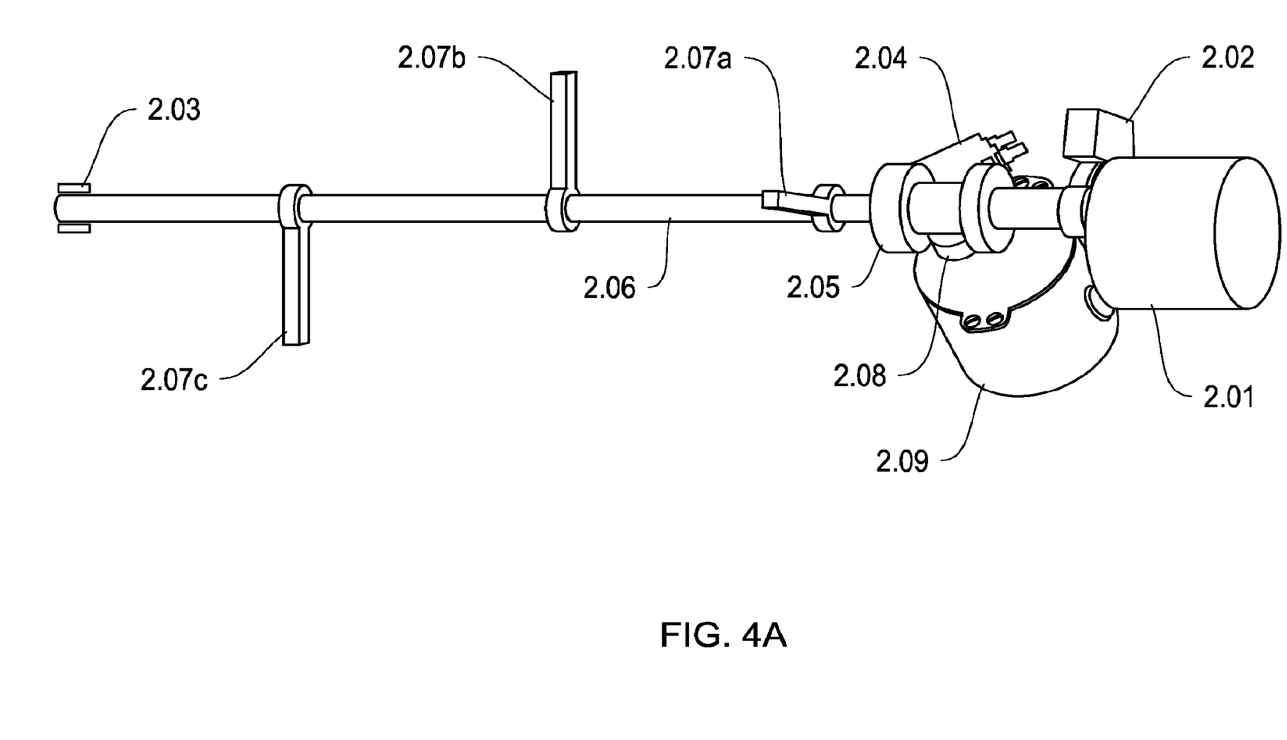
FIG. 4a is a perspective view of one embodiment of a single valve drive unit.

FIG. 4 illustrates a valve assembly unit that includes six three valves blocks 2.10 and a valve drive mechanism 2.00 that designed to activate all valves 2.10. FIG. 4a discloses in greater details the preferred design of the drive mechanism. According to the program, motor 2.01 rotates the shaft 2.06 in a position where the pad 2.07a is exactly opposite one of the valve actuation bar, for example, FIG. 5, position 07. The shaft 2.06 is fixed with cam 2.05 and mounted in bearing 2.03 with the possibility of axial motion. Next, motor 2.09 rotates the cam 2.08 and pushes the cam 2.05 with the shaft 2.03 forward, and pad 2.07a farther pushes the actuation bar 07 (FIG. 5).

Figure 5:
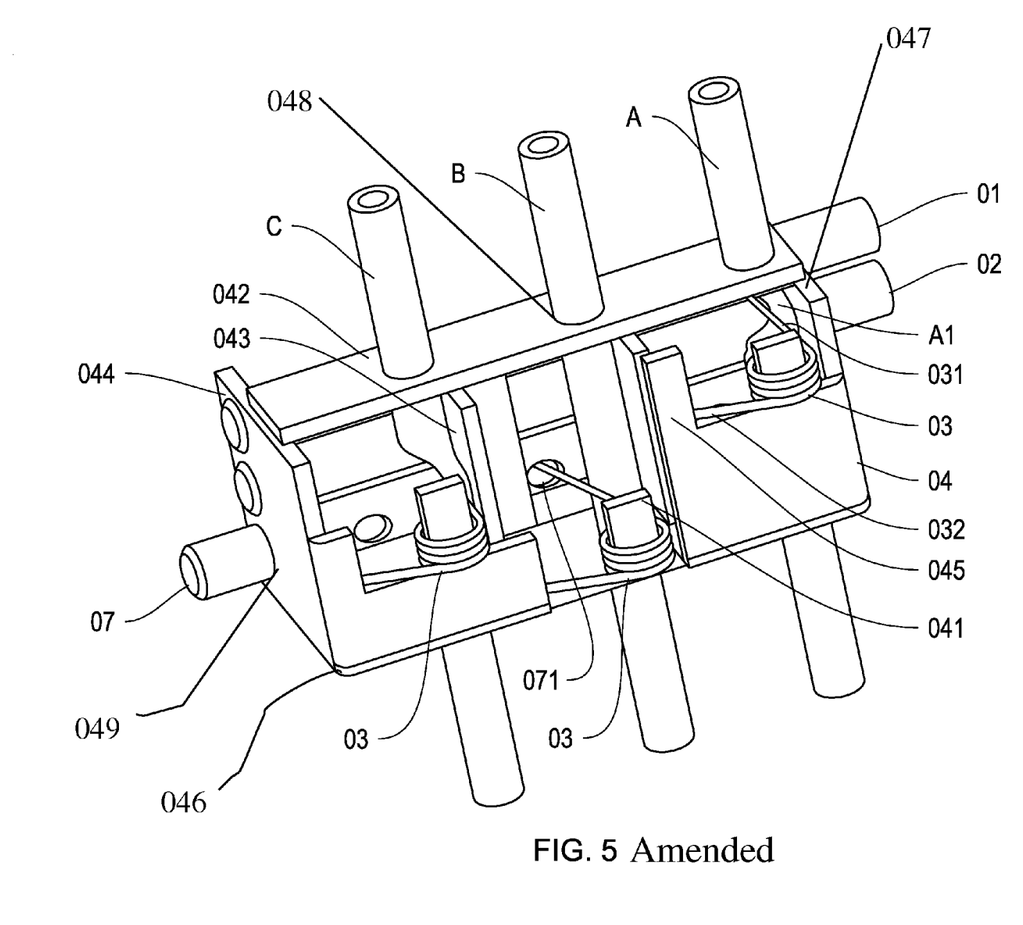
FIG. 5 is a perspective view of one embodiment of a 3 pinch valves assembly used with a single drive unit.

FIG. 5 illustrates the exemplary design of the valves. The valve body 04 has a number, corresponding to the number of valves, studs, designated 041, passageways 048 and rigid vertical abutments 043, and one of three guide-way holes 049 shown on left flange 044. Flexible flow conduits, designated A, B, and C threaded through passageways 048 located on upper flange 042 and seen only for flow conduit B. Round elongated members 01, 02, and 07 are threaded with possibility to move along their axes through three guide-way holes shown in left support flange 044. Torsion springs designated 03 are loosely seated on studs 041, with one leg designated 032 fixed against lugs 045 of the housing; while the other leg 031 directed perpendicular to the conduit's axis, pinches the conduit by pressing it to the abutment 043, as seen with reference to FIG. 5 forming the pressed part of the conduits A1 preventing the fluid flow. Further these legs extend through the holes in the elongated members 01, 02, and 07, seen only with elongated member 07, designated as 071. As seen with reference to FIG. 5 when the elongated members 07 is moved forward, the torsion spring 03 released the conduit B, opening the elastic conduit going thru passageway and fluid flow.

Figure 5A:
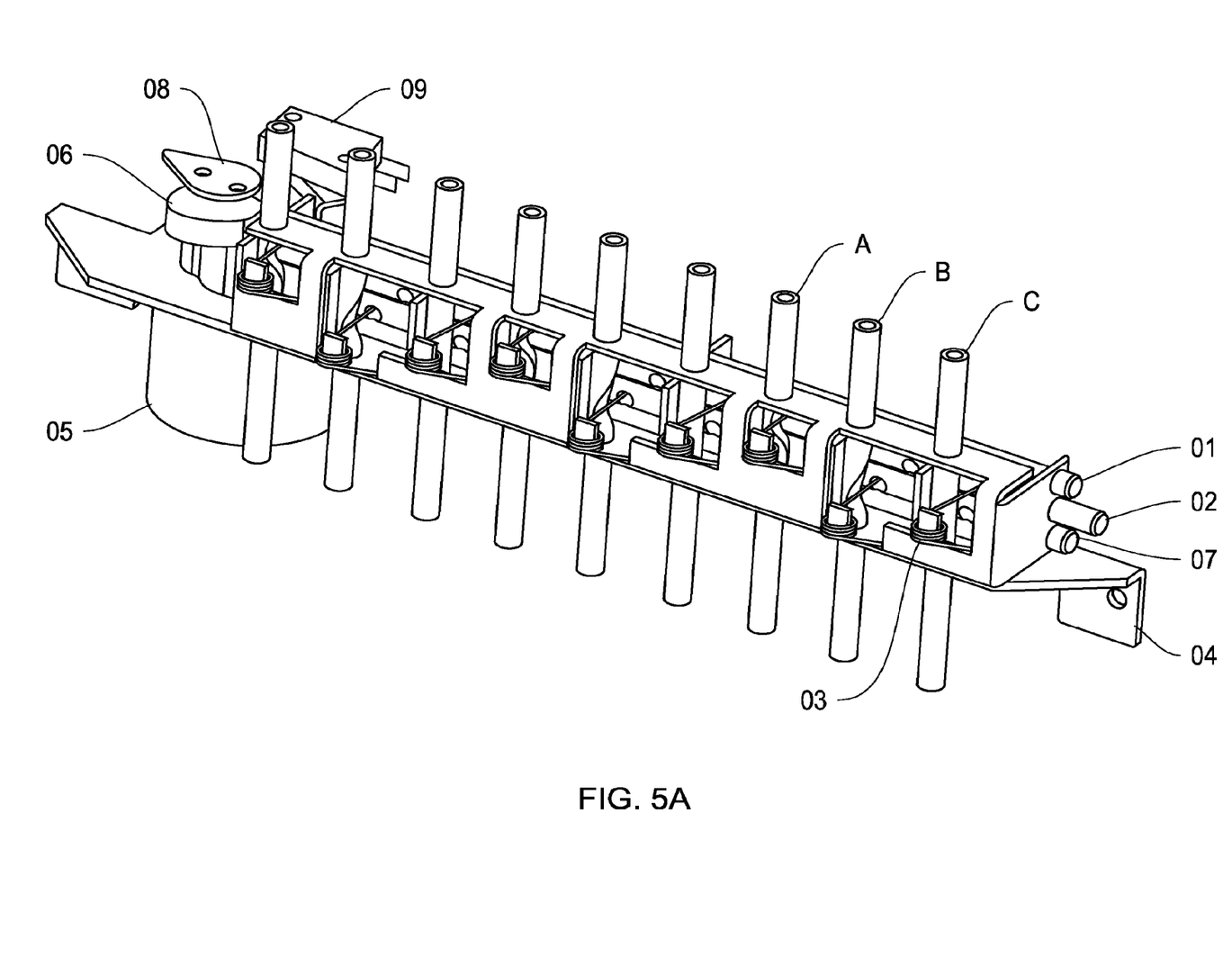
FIG. 5a is a perspective view of an exemplary embodiment of a block of 9 pinch valves uses with individual drive unit.
Figure 5B:
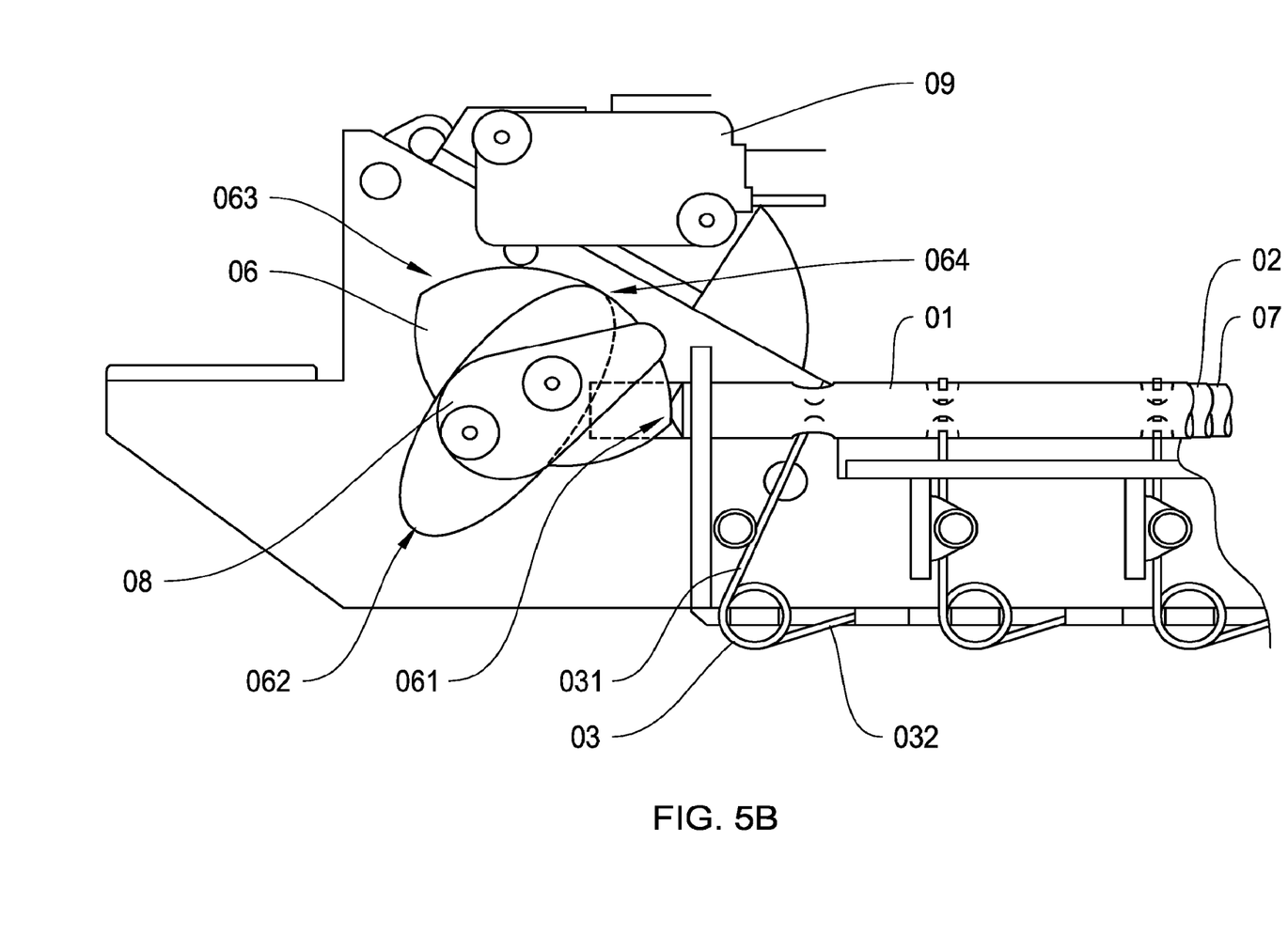
Figure 5C:
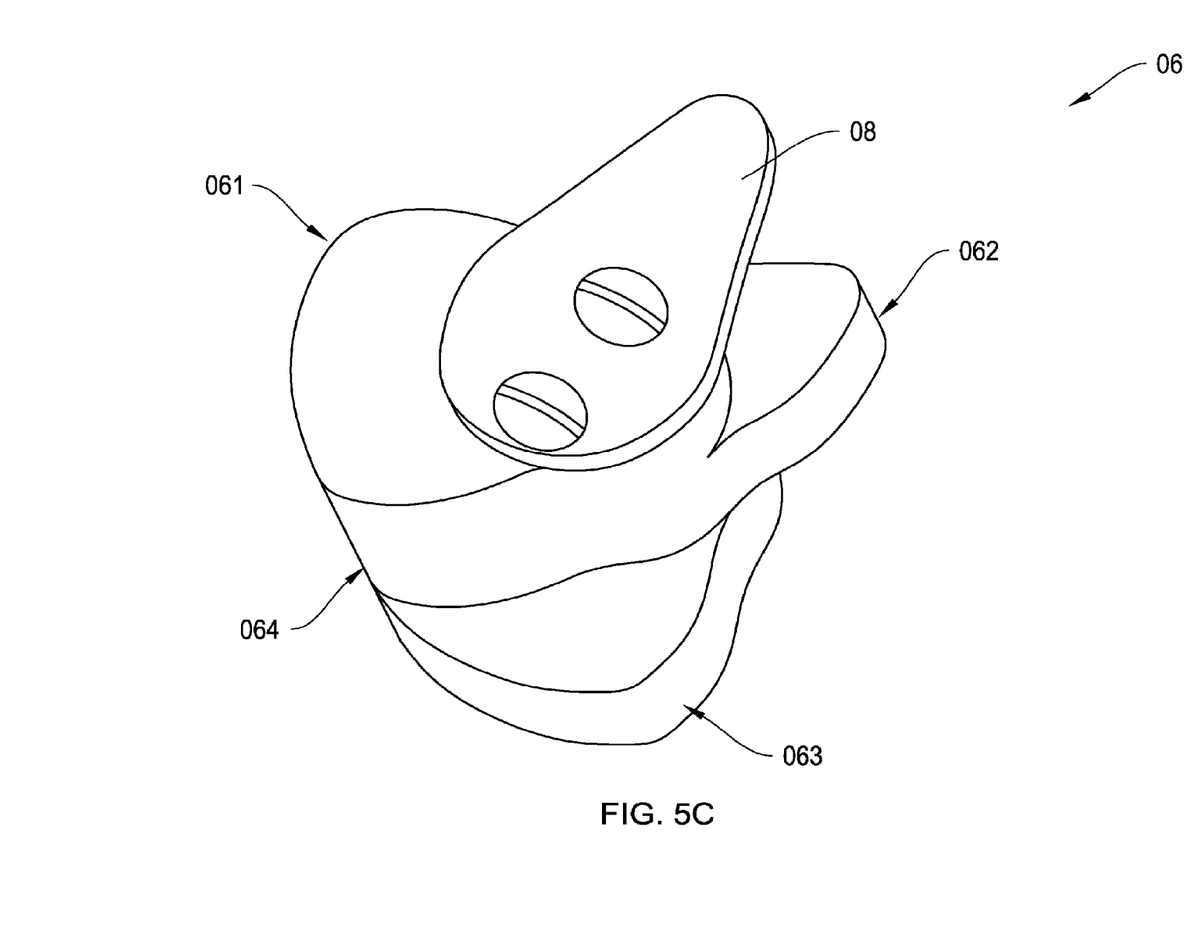

As seen with reference to FIGS. 5a, 5b, and 5c that different surface of the cam 06, 061, 062, 063, or 064 facing three elongated members 01, 02, and 07. Thus, rotation of the cam in either direction causes different independent displacement of each elongated member, which in turn release or press the movable legs 031 of the torsion springs allow rotation of the spring 03 around the stud 041 and compress or release the conduit, allowing the liquid flow or close independently for each set of conduits. The time to rest of the cam in each position determines the volume of fluid flow through the conduit. The position to rotate, the sequence, and time may be easy programmed.

Figure 6:
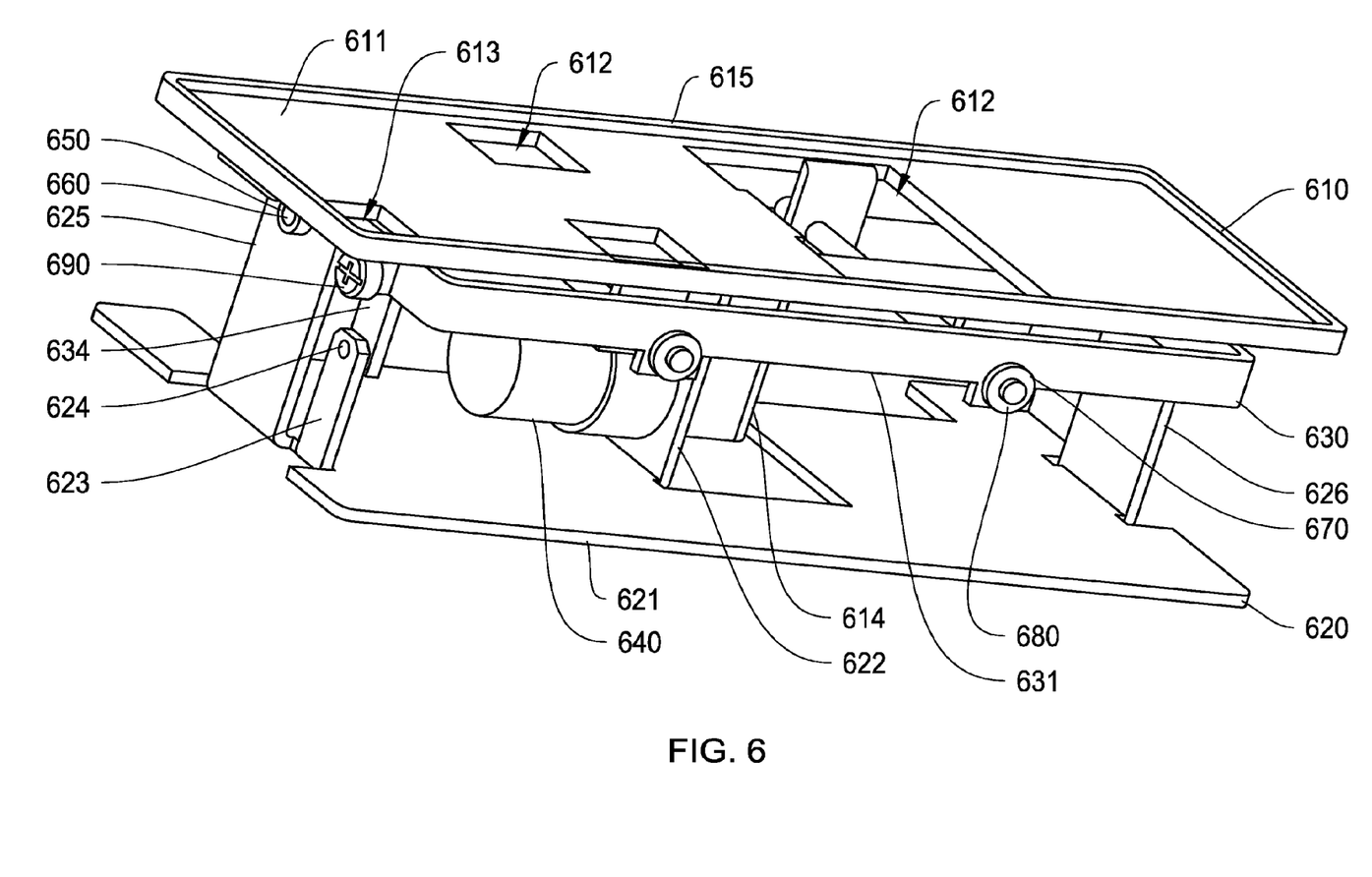
FIG. 6 is a perspective view of an agitating table that can alternatively be set up for a rocking or a shaking movement of tray platform.

FIG. 6 is illustrates the agitating table 6. There are four major parts: 610—is tray support platform, 620—is a base, 630—is a rocking bracket, and 640—agitating motor. Base 620 contains a flat bottom 621 from which extended two protrusions 625 and 626 that support the bearings 650, a protrusion 622 that supports agitating motor 640, and protrusion 623 that serves to fix the rocking bracket to the base when the back-and-forth motion of the trays is set up. Tray platform 610 contains a flat part 611 from which extended four protrusions 612 that are serving as supports for two guide bars 680 that fixed to platform, and protrusion 613 serving to fix the platform to the rocking bracket when the rocking motion of the platform is set up. The agitating motor 640 holds an eccentric cam, not shown, that engaged with C shape protrusion 614. The rib 615 is used to hold in place one or multiple of trays. The rocking bracket 630 holds four bearings 670 which allow the guiding bars 680 and the tray's platform slide back-and-forth. Protrusion 634 serves to fix the rocking bracket 630 either to base 620 or to trays platform 610 changing the type of agitation. For this purpose the special screw 690 may be engaged with threaded hole in the rocking bracket body or installed in the hole 624 in protrusion 623 and screwed up with rocking bracket.

As described heretofore, the present invention is directed to an automated assay apparatus comprising one or multiple assay blocks each of them contains liquid reagents and washer vessels and a tray to support reactant, each of them sealed after filling to be ready for performing assay procedure. The apparatus further comprises means to automatically deliver said reagents and washer liquids into tray of the said block and discharge the reagent and washer liquids from tray into designated vessels in pre-programmed order, for each block independent from others. The apparatus further comprises means providing pre-installed, as desired, horizontal shaking or rocking movements of trays. The apparatus further comprises control means to activate the means to automatically deliver and discharge said liquids to and from each tray undependably, according to preprogrammed sequence. The apparatus further comprises means to control the volume of washing liquid supplied to supply vessels and trays. The vessels and trays comprise a kind of kegs, different sizes and shapes, with sealed lids, connected to each other and to air supply by elastomeric flow conduits and valves. The vessels and trays, in order to facilitate the liquid flow, are supplied with positive air pressure, with simultaneously opening the target vessels' air line to atmosphere. The means to shake trays horizontally or rock them around horizontal axis comprise two guides, a horizontal cross guide-way and a longitudinal axis with bearings, a set of parts to lock either motion, and a DC gear motor with a cam drive. The trays' motions are set up the rocking motion of the trays by locking together rocking bracket and the tray platform, and to set up the horizontal agitating motion of the trays the rocking bracket is locked to the base, unlocking the tray's platform. The means to control the volume of washing liquid comprise sealed chambers, having moving pistons used to pre-install the chambers volume. The chambers are connected to the air line and atmosphere through automatically controlled valves. The valves comprise elastomeric flow conduits initially completely closed by torsion springs that pressing the walls of fluid conduits together onto rigid abutments and serving as pinch members. The means to automatically deliver said reagents and washer liquids into tray of the said block and discharge the reagent and washer liquids from the said trays is a multiple of programmable pinch valves assemblies for control delivery of multiple different fluids from sources to sites by pinching or releasing of elastomeric flow conduits comprising: a housing with plural studs and passageways, multiple elastomeric flow conduits that are threaded through housing passageways, actuator means located in and movable within the housing for acting against the forces of torsion springs to open selected fluid conduits. The valve assembly housing contains plural studs and passageways, and guides as a number of holes in two opposite walls of the housing. The torsion springs are loosely seated on said studs with one leg fixed to the housing, wile the other leg, directed perpendicular to the tube's axis, selectively and individually pinching the conduits preventing the fluid flow. Further this leg extends through the hole in the bar. The torsion springs are loosely seated on the studs to allow easy pivoting the spring around the stud and easy removing it when necessary to change. The backing means are a number of abutments of the housing comprising the vertical walls adjacent to the passageways for elastomeric fluid conduits providing sufficient resistance to accomplish complete closing of the fluid flow through the conduits. The abutments comprise substantially parallel surfaces for support fluid conduits. The studs and spring retaining lugs of the housing placed raw over raw according the number of sets of simultaneously activated multiple of elastomeric flow conduits. The actuator means comprise bars having holes normal to the bar's axis, threaded through and movable along the said housing guide ways. The actuator means comprising bars with holes normal to the bar axis, threaded through and movable along the said housing guideways, engaged with the said torsion spring threaded through the said holes. The means to automatically deliver said reagents and washer liquids into tray of the said block and discharge the reagent and washer liquids from the said trays is a multiple of programmable pinch valves assembly for control delivery of multiple different fluids from sources to sites by pinching or releasing of elastomeric flow conduits further comprising a actuator drive that comprise: a shaft located along housing body, a motor that rotates the shaft, a motor with a cam to supply longitudinal motion to the shaft and electrical switches to control the shaft's motions. The shaft bears a number of pads located near actuator's end, said pads translate the shaft's motion, by contacting, to the selecting actuator, to forth the engaged torsion spring to release selected elastomeric flow conduits. The means to automatically deliver said reagents and washer liquids into tray of the said block and discharge the reagent and washer liquids from the said trays is a multiple of programmable pinch valves assembly for control delivery of multiple different fluids from sources to sites by pinching or releasing of elastomeric flow conduits further comprising a actuator drive that comprise: attached to the housing motor and rotatable cam, mounted on the motor's shaft, one or more actuator means, parallel to each other and perpendicular to the cam's axis of rotation, engaged with a number of torsion springs used as a pinch member. The cam has extending radial protrusions which form a cam profile—a displacement profile which placed along the axis of the cam and form a multi track cam, the number of tracks corresponds to the number of flow conduit sets. The cam rotated in either direction imparts the translating motion to the actuator bars which, due to the special contour of said displacement profile, may slide either simultaneously all together or individually in a programmable sequences. When the bar moves it pushes the engaged springs away from the conduits releasing the fluid flow. The valve is programmable by tracks profiles, sequence of cam rotation directions, and the duration of the rotation. The cam actuator contains a number of displacement profiles for activating the movement of cam followers according to desired sequence, activating only one. The cam actuator contains an addition profile track that engaged with electric switch to control the initial position of the cam. The cam followers may contact the cam's displacement profile directly or through intermediate member such as lever, protection.

As described heretofore, the present invention is also directed to a method for automatically deliver reagents and washer liquids into tray and discharge the reagent and washer liquids from the said trays comprising a multiple of programmable pinch valves assembly for control delivery of multiple different fluids from sources to sites by pinching or releasing of elastomeric flow conduits comprising means to automatically deliver said reagents and washer liquids into tray of the said block and discharge the reagent and washer liquids from the said trays is a multiple of programmable pinch valves assembly for control delivery of multiple different fluids from sources to sites by pinching or releasing of elastomeric flow conduits comprising: a housing with plural studs and passageways, multiple elastomeric flow conduits that are threaded through housing passageways, actuator means located in and movable within the housing for acting against the forces of torsion springs to open selected fluid conduits. The means to automatically deliver said reagents and washer liquids into tray of the said block and discharge the reagent and washer liquids from the said trays is a multiple of programmable pinch valves assembly for control delivery of multiple different fluids from sources to sites by pinching or releasing of elastomeric flow conduits comprising: torsion springs serving as a pinch members, contacting the walls of elastomeric flow conduits and pressing them together onto rigid abutments. The means to automatically deliver said reagents and washer liquids into tray of the said block and discharge the reagent and washer liquids from the said trays is a multiple of programmable pinch valves assembly for control delivery of multiple different fluids from sources to sites by pinching or releasing of elastomeric flow conduits comprising: a housing with plural studs and passageways, multiple elastomeric flow conduits that are threaded through housing passageways, actuator means located in and movable within the housing for acting against the forces of torsion springs to open selected fluid conduits. The valves assembly housing contains plural studs and passageways, and guides as a number of holes in two opposite walls of the housing. The torsion springs are loosely seated on said studs with one leg fixed to the housing, wile the other leg, directed perpendicular to the tube's axis, selectively and individually pinching the conduits preventing the fluid flow. Further this leg extends through the hole in the bar. The torsion springs are loosely seated on the studs to allow easy pivoting the spring around the stud and easy removing it when necessary to change. The backing means are a number of abutments of the housing comprising the vertical walls adjacent to the passageways for elastomeric fluid conduits providing sufficient resistance to accomplish complete closing of the fluid flow through the conduits. The abutments comprise substantially parallel surfaces for support fluid conduits. The studs and spring retaining lugs of the housing placed raw over raw according the number of sets of simultaneously activated multiple of elastomeric flow conduits. The actuator means comprising bars having holes normal to the bar's axis, threaded through and movable along the said housing guide-ways. The actuator means comprise bars with holes normal to the bar axis, threaded through and movable along the said housing guideways, engaged with the said torsion spring threaded through the said holes.

The foregoing description is intended for purposes of illustration. The invention may be embodied in other forms or carried out in other ways without departing from the spirit or scope of the invention.

What is claimed:

1. An automated assay apparatus for performing one or more assay procedures using a liquid reagent and a washer liquid, the apparatus comprises:
    a first reagent supply vessel adapted to be filled with the liquid reagent;
    a first reaction chamber;
    a first elastomeric conduit comprising, a first end in communication with said first reagent supply vessel, and a second end in communication with said first reaction chamber; and
    a valve chassis operable with said first elastomeric conduit to deliver said liquid reagent from said first reagent supply vessel to said first reaction chamber; said valve chassis comprises upper and lower flanges and left and right support flanges; said valve chassis further comprises a first valve having a vertical abutment extending between said lower and upper flanges of said valve chassis; said first valve further comprises a passageway formed in said upper and lower flanges of said valve chassis; said first elastomeric conduit extends thru said passageway; said first valve further comprises a spring having a first leg engaged with lug and a second leg having an end portion; said second leg of said spring is normally biased to pinch said first elastomeric conduit against said vertical abutment to close said first elastomeric conduit to prevent delivery of the liquid reagent to said first reaction chamber.

2. The apparatus of claim 1, wherein said valve chassis further comprises a first guide-way hole formed in said left support flange and a first guide-way hole formed in said right support flange; said first guide-way hole of said left flange being substantially aligned with said first guide-way hole of said right support flange.

3. The apparatus of claim 2, wherein said valve chassis further comprises a first elongated member having first and second ends and a body portion; said first end of said first elongated member extends thru and outward of said first guide-way hole of said left support flange; said second end of said first elongated member extends thru and outward of said first guide-way hole of said right support flange; said first elongated member further comprises an opening to receive said end portion of said second leg of said spring of said first valve; movement of said first elongated member causes movement of said second leg of said spring of said first valve thereby opening said passageway of said first elastomeric conduit.

4. The apparatus of claim 3, wherein said side flange of said first valve comprises a stud;
    said spring of said first valve is loosely seated on said stud to allow substantial pivoting of said spring of said first valve around said stud of said first valve and removal of said spring of said first valve.

5. The apparatus of claim 4, further comprising a drive mechanism adapted to move said elongated member.

6. The apparatus of claim 5, wherein said drive mechanism comprises a motor, a shaft, and a cam engaged with said shaft; rotation of said shaft causes rotation of said cam.

7. The apparatus of claim 6, wherein said cam comprises a first cam surface that engages with said first end of said first elongated member.

8. The apparatus of claim 3, wherein said side flange of said second valve comprises a stud;
said spring of said second valve is loosely seated on said stud of said second valve to allow substantial pivoting of said spring of said second valve around said stud of said second valve and removal of said spring of said second valve.

9. The apparatus of claim 8, wherein said cam comprises a second surface that engages with said first end of said second elongated member.

10. The apparatus of claim 9, wherein each of said first and second elongated members is a plastic rod.

11. The apparatus of claim 10, wherein each of said springs of said first and second valves is a torsion spring.

12. The apparatus of claim 1, further comprising a washer supply vessel filled with a washer liquid; a variable volume measure vessel in communication with said washer supply vessel to control the volume of said washing liquid supplied to said first reagent supply vessel and said first reaction chamber; and a second elastomeric conduit comprising a first end in communication with said variable volume measure vessel, and a second end in communication with said first reaction chamber.

13. The apparatus of claim 12, wherein said valve chassis further comprises a second guide-way hole formed in said left support flange and a second guide-way hole formed in said right support flange; said second guide-way hole of said left support flange being substantially aligned with said second guide-way hole of said right support flange.

14. The apparatus of claim 13, wherein said valve chassis further comprises a second valve having a lug and an abutment extending between said lower and upper flanges of said valve chassis; said second valve further comprises a passage way formed in said upper and lower flanges of said valve chassis; said second elastomeric conduit extends thru said passageway of said second valve; said second valve further comprises a spring having a first leg engaged with said lug of said second valve and a second leg having an end portion; said second leg of said spring of said second valve is normally biased to pinch said second elastomeric conduit against said vertical abutment of said second valve to close said passageway of said second elastomeric conduit to prevent delivery of said washer liquid to said first reaction chamber.

15. The apparatus of claim 14, wherein said valve chassis further comprises a second elongated member having first and second ends and a body portion; said first end of said second elongated member extends thru and outward of said second guide-way hole of said left support flange; said second end of said second elongated member extends thru and outward of said second guide-way hole of said right support flange; said second elongated member further comprises an opening to receive said end portion of said second leg of said spring of said second valve; movement of said second elongated member causes movement of said second leg of said spring of said second valve thereby opening said passageway of said second elastomeric conduit.

* * * * *